United States Patent
Nakayama

(10) Patent No.: US 9,966,523 B2
(45) Date of Patent: May 8, 2018

(54) ACOUSTIC SENSOR AND ULTRASOUND PROBE

(71) Applicant: KONICA MINOLTA, INC., Chiyoda-ku, Tokyo (JP)

(72) Inventor: Yuta Nakayama, Ichikawa (JP)

(73) Assignee: KONICA MINOLTA, INC., Tokyo (JP)

( * ) Notice: Subject to any disclaimer, the term of this patent is extended or adjusted under 35 U.S.C. 154(b) by 456 days.

(21) Appl. No.: 14/634,419

(22) Filed: Feb. 27, 2015

(65) Prior Publication Data

US 2015/0263261 A1    Sep. 17, 2015

(30) Foreign Application Priority Data

Mar. 13, 2014    (JP) .................................. 2014-049720

(51) Int. Cl.
  *H01L 41/04*    (2006.01)
  *H01L 41/08*    (2006.01)
  *H01L 41/113*   (2006.01)
  *A61B 8/00*     (2006.01)

(52) U.S. Cl.
  CPC .......... *H01L 41/042* (2013.01); *A61B 8/4483* (2013.01); *A61B 8/4494* (2013.01); *H01L 41/0805* (2013.01); *H01L 41/1132* (2013.01)

(58) Field of Classification Search
  CPC ............... H01L 41/042; H01L 41/0805; H01L 41/1132; A61B 8/4483; H03H 9/175; G10K 11/18
  USPC ......................................... 310/334, 335, 336
  See application file for complete search history.

(56) References Cited

U.S. PATENT DOCUMENTS

| | | | |
|---|---|---|---|
| 3,832,700 A | 8/1974 | Wu et al. | |
| 5,160,870 A * | 11/1992 | Carson | ................. B06B 1/0629 310/324 |
| 5,225,705 A | 7/1993 | Satoshi et al. | |
| 2008/0266004 A1* | 10/2008 | Denier | .................. H01L 41/042 331/1 A |
| 2011/0121765 A1* | 5/2011 | Anderson | ............... G06F 3/016 318/116 |

(Continued)

FOREIGN PATENT DOCUMENTS

| JP | 48058795 A | 8/1973 |
|---|---|---|
| JP | 04305131 A | 10/1992 |
| JP | 09264799 A | 10/1997 |

OTHER PUBLICATIONS

Japanese Office Action dated Nov. 28, 2017 issued in counterpart Japanese Application No. 2014-049720.

*Primary Examiner* — Bryan Gordon
(74) *Attorney, Agent, or Firm* — Holtz, Holtz & Volek PC

(57) ABSTRACT

Disclosed is an acoustic sensor including a semiconductor chip comprising two or more transistors. At least two of the transistors are each connected to a piezoelectric thin film, and the piezoelectric thin film is directly or indirectly disposed over a semiconductor substrate such that a conduction state of each of the at least two transistors varies in response to a pressure of sound waves incident on the piezoelectric thin film, and the two or more transistors are connected to constitute a single amplifier circuit so as to add up and amplify a signal with a strength in response to the conduction state of each of the at least two transistors, and output the amplified signals.

7 Claims, 3 Drawing Sheets

(56) References Cited

U.S. PATENT DOCUMENTS

| | | | |
|---|---|---|---|
| 2011/0228389 A1* | 9/2011 | Ohashi | G02B 27/0006 359/507 |
| 2012/0108963 A1* | 5/2012 | Hara | H03K 17/063 600/437 |
| 2014/0070666 A1* | 3/2014 | Muggler | H01L 41/042 310/314 |
| 2014/0327378 A1* | 11/2014 | Van Rens | H01L 41/042 318/116 |

* cited by examiner

ACOUSTIC SENSOR AND ULTRASOUND PROBE

BACKGROUND OF THE INVENTION

1. Field of the Invention

The present invention relates to an acoustic sensor and an ultrasound probe.

2. Description of the Related Art

A conventional ultrasound diagnosis apparatus irradiates the interior of a subject with ultrasound waves, receives echoes reflected from the interior and analyzes the reflected echoes to examine the internal structure of the subject. Ultrasound diagnosis apparatuses are widely used for various purposes such as medical examination and inspection of the interior of buildings and structures since ultrasound diagnoses can nondestructively and noninvasively determine the states of subjects.

An ultrasound diagnosis apparatus converts received ultrasound waves into electric signals having strengths in relation to the intensities of the received ultrasound waves, and acquires the electric signals. An acoustic sensor for receiving such ultrasound waves includes transducers having piezoelectric elements. The sound pressure of ultrasound waves causes the piezoelectric elements to be mechanically deformed (expansion and contraction). The ultrasound diagnosis apparatus converts the deformation of each piezoelectric element into an electric signal (the amount of electric charge) having a strength in relation to the amount of the deformation, and detects the converted electric signal. In such a conventional acoustic sensor, transducers containing piezoelectric elements are formed into a plate or thick film or a multilayer substrate with a thickness of 10 μm or more in ordinary cases and 100 μm or more in general by, for example, a thick film coating technique. The ultrasound diagnosis apparatus detects deformation of each piezoelectric element in the direction of thickness, which is caused by ultrasound waves incident on a surface of this plate-like transducer, to determine the intensities of the ultrasound waves.

The piezoelectric element contains a ferroelectric material, such as lead (Pb) zirconate titanate (PZT). The ferroelectric material, which has polarization characteristics with hysteresis, has been used for nonvolatile memory (ferroelectric random access memory, FeRAM). U.S. Pat. No. 3,832,700 discloses a ferroelectric memory having a ferroelectric thin film between a gate electrode and a channel region separating a source and a drain. A voltage is applied to the ferroelectric thin film to alter electrical conductivity in the channel region so that the polarization characteristics corresponding to either of two values are kept. The state of conduction between the drain and the source is measured to read the two values.

Development of ultrasound diagnosis apparatuses with higher resolution and sensitivity needs ultrasound probes with higher precision. Unfortunately, a more complicated production process, a larger acoustic sensor, and increased process and labor costs are inevitable to acquire more efficiently electric signals from a piezoelectric component in an acoustic sensor used for receiving ultrasound waves in a conventional ultrasound probe in ordinal manners.

SUMMARY OF THE INVENTION

It is an object of the present invention to provide an acoustic sensor and an ultrasound probe that can efficiently acquire signals from a piezoelectric component at higher precision without increases in process and labor costs.

In order to realize at least one object, an acoustic sensor reflecting one aspect of the present invention includes a semiconductor chip comprising two or more transistors, wherein at least two of the transistors are each connected to a piezoelectric thin film, and the piezoelectric thin film is directly or indirectly disposed over a semiconductor substrate such that a conduction state of each of the at least two transistors varies in response to a pressure of sound waves incident on the piezoelectric thin film, and wherein the two or more transistors are connected to constitute a single amplifier circuit so as to add up and amplify a signal with a strength in response to the conduction state of each of the at least two transistors, and output the amplified signals.

The thin film is formed by a sputtering process, a chemical-vapor deposition (CVD) process, a sol-gel process, or any other thin film fabrication process.

In the acoustic sensor, preferably, the semiconductor chip further comprises a circuit for applying a predetermined bias voltage to the piezoelectric thin film, and the bias voltage is determined such that the strength of a signal output through each of the at least two transistors is complementary with respect to the pressure of sound waves incident on the piezoelectric thin film.

In the acoustic sensor, preferably, each of the piezoelectric thin films is formed of a ferroelectric material, and polarizations of the piezoelectric thin films are determined such that the strengths of signals in response to the respective pressures of sound waves incident on the respective piezoelectric thin films are complementary.

In the acoustic sensor, preferably, the at least two transistors are two field-effect transistors in which each field-effect transistor includes the piezoelectric thin film between a gate electrode and a channel region, and wherein drains of the field-effect transistors are connected to each other such that each field-effect transistor constitutes a common-source amplifier circuit, and signals are output through the drains.

An ultrasound probe in accordance with an aspect of the present invention includes the acoustic sensor described above.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

An embodiment of the present invention will now be described with reference to the attached drawings.

Figure 1:
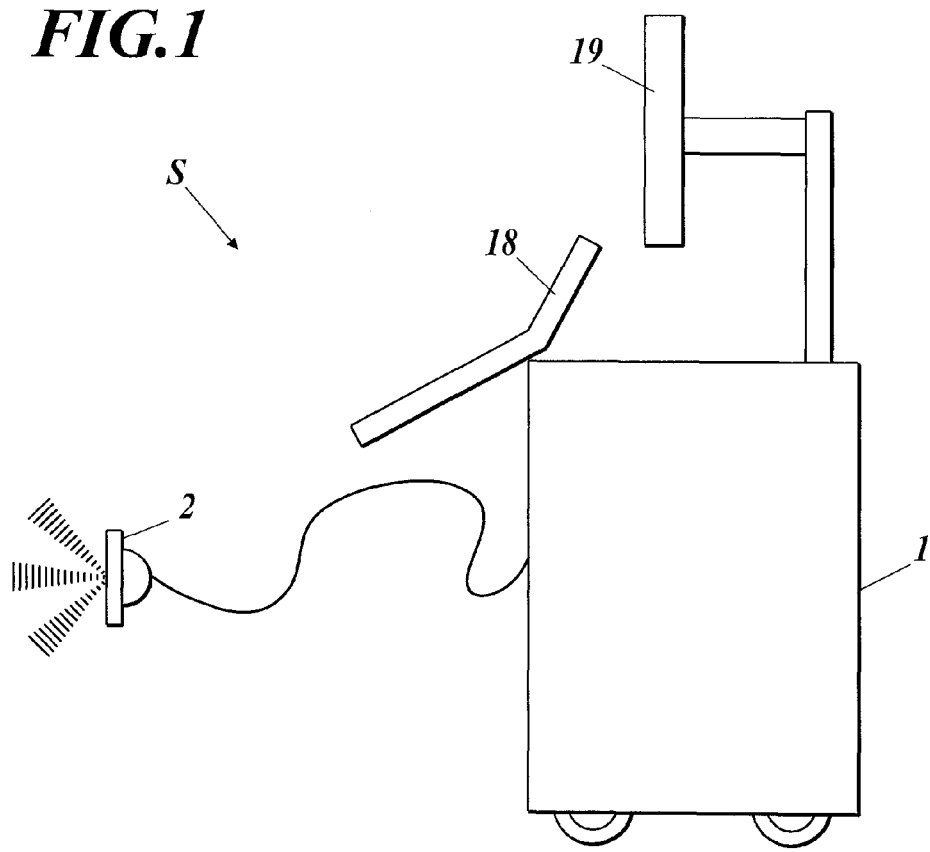
FIG. 1 is an overall view of an ultrasound diagnosis apparatus in accordance with an embodiment of the present invention.
Figure 2:
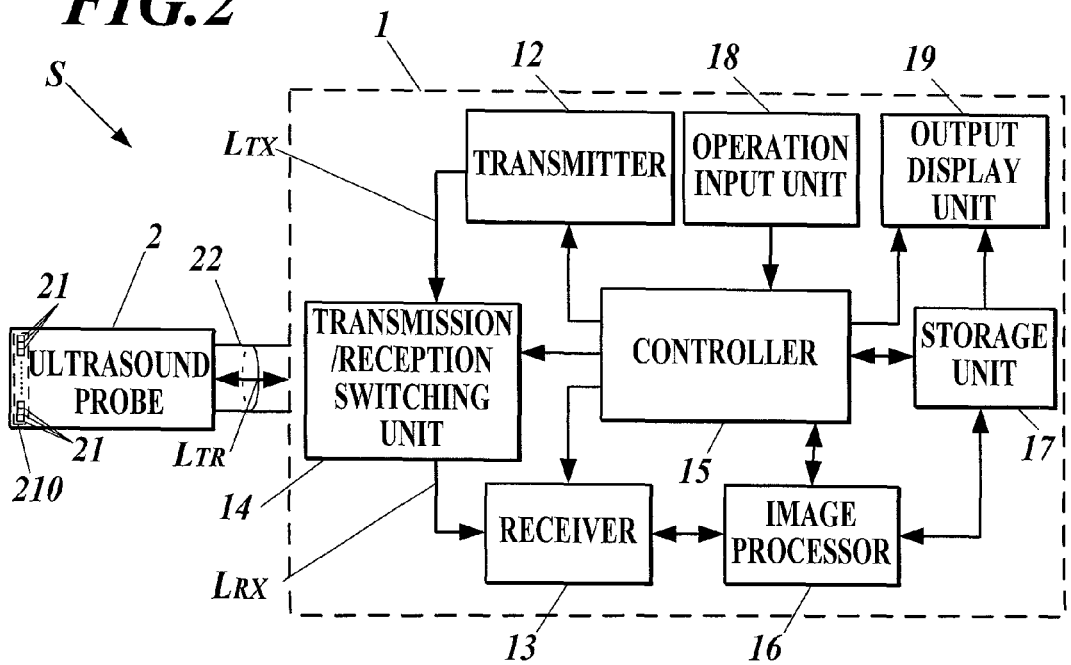
FIG. 2 is a block diagram illustrating an internal configuration of the ultrasound diagnosis apparatus.

FIG. 1 is an overall view of an ultrasound diagnosis apparatus S equipped with an ultrasound probe 2 including an acoustic sensor according to this embodiment. FIG. 2 is a block diagram illustrating an internal configuration of the ultrasound diagnosis apparatus S.

With reference to FIG. 1, the ultrasound diagnosis apparatus S includes a main unit 1 and the ultrasound probe 2 connected to the main unit 1 via a cable 22. The main unit 1 is equipped with an operation input unit for operation of the apparatus and an output display unit 19 for output of the results. According to an input from external input devices, such a keyboard and a mouse included in the operation input unit, a controller 15 in the main unit 1 outputs a driving signal to the ultrasound probe 2 to cause the ultrasound probe 2 to output ultrasound waves. The ultrasound probe 2 also receives ultrasound waves. The controller 15 acquires signals in response to the received ultrasound waves from the ultrasound probe 2 and performs operations. The controller 15 then displays the results and/or other data on a liquid crystal or any other screen in the output display unit 19 as needed.

With reference to FIG. 2, the main unit 1 includes a transmitter 12, a receiver 13, a transmission/reception switching unit 14, the controller 15, an image processor 16, a storage unit 17, the operation input unit, and the output display unit 19.

According to a control signal sent from the controller 15, the transmitter 12 supplies pulse signals to the ultrasound probe 2 to cause the ultrasound probe 2 to generate ultrasound waves. The transmitter 12 includes, for example, a clock circuit, a pulse circuit, a pulse width determiner, and a delay circuit. The clock circuit generates clock signals which determine the timing and the frequency of transmitted pulse signals. The pulse circuit generates bipolar rectangular pulses with a predetermined voltage or amplitude in a given cycle. The pulse width determiner sets the width of rectangular pulses transmitted from the pulse circuit. Rectangular pulses generated at the pulse circuit are separated into different wiring paths for respective transducers 21 in the ultrasound probe 2 either before or after the rectangular pulses enter the pulse width determiner. In response to a timing with which generated rectangular pulses are transmitted to the transducers 21, the delay circuit delays the transmission of the pulses by individual delay times set for the respective wiring paths.

The receiver 13 is a circuit for acquiring signals sent from the ultrasound probe 2 under the control of the controller 15. The receiver 13 includes, for example, an amplifier, an analog-to-digital (A/D) converter, and a phasing addition circuit. The amplifier is a circuit for amplifying individual signals in response to respective ultrasound waves received at the respective transducers 21 in the ultrasound probe 2 by a predetermined amplification factor. The A/D converter converts the amplified signals into digital data at a predetermined sampling frequency. The phasing addition circuit phases the A/D converted signals by giving individual delay times to the respective wiring paths for the respective transducers 21, and adds up the phased signals to create sound ray data.

The transmission/reception switching unit 14 switches transmission and reception operations under the control of the controller 15. The transmitter 12 sends driving signals to the transducers 21 so that the transducers 21 emit ultrasound waves, while the receiver 13 transmits receiving signals to the transducers 21 so that the receiver 13 acquire signals in response to ultrasound waves received at the transducers 21, through operation of the transmission/reception switching unit 14.

The controller 15 includes a central processing unit (CPU), a hard disk drive (HDD), and a random access memory (RAM). The CPU reads programs stored in the HDD and loads them onto the RAM. Under instruction of the loaded programs, the CPU comprehensively controls the operation of each component in the ultrasound diagnosis apparatus S. The HDD stores control programs and processing programs for operating the ultrasound diagnosis apparatus S, and various setting data and other information. These programs and setting data may be stored, for example, in any readable and rewritable auxiliary storage devices composed of nonvolatile memory such as flash memory, other than the HDD. The RAM is static random access memory (SRAM), dynamic random access memory (DRAM), or any other volatile memory. The RAM provides working area for the CPU and stores temporary data.

The image processor 16 includes a processor module, which is separate from the CPU of the controller 15. The image processor 16 performs arithmetic operations to generate diagnostic images based on data received through ultrasound waves. The diagnostic images include image data and video data composed of a series of still images, which are displayed on the output display unit 19 in roughly real time, and still images of snapshots. The arithmetic operations may be performed by the CPU of the controller 15.

The storage unit 17 is, for example, DRAM or any other volatile memory. Alternatively, the storage unit 17 may be any kind of nonvolatile memory which allows rewriting data at high speeds. The storage unit 17 stores diagnostic image data for real-time display, which is processed at the image processor 16, in units of frames. Under the control of the controller 15, image data for ultrasound diagnosis stored in the storage unit 17 is read, and is sent to the output display unit 19 or output to the exterior of the ultrasound diagnosis apparatus S via a communication unit (not shown). If the output display unit 19 is based on a television system to display data, a digital signal converter (DSC) should be provided between the storage unit 17 and the output display unit 19 so that the scanning format of image data is converted and then the image data is sent to the output display unit 19.

The operation input unit includes a push button switch, a keyboard, and either a mouse or a trackball, or a combination thereof. The operation input unit converts an input operation by the user to an operation signal and inputs the operation signal into the main unit 1.

The output display unit 19 includes a screen and a drive unit therefor. The display is any one of a liquid crystal display (LCD), an organic electroluminescent (OEL) display, an inorganic electroluminescent display, a plasma display, a cathode ray tube (CRT) display, and any other display. In accordance with control signals output from the CPU of the controller 15 and image data generated by the image processor 16, the output display unit 19 produces signals for driving the display screen (picture elements) to display a menu and a status indication depending on the ultrasound diagnosis and measurements obtained through received ultrasound waves on the screen.

The operation input unit and the output display unit 19 may be integrated with the main unit 1, or may be disposed externally and connected to the main unit 1 via USB cables or any other connector. Alternatively, if the main unit 1 includes terminals for operational input and display output, the operation input unit and the output display unit 19 can be conventional peripheral devices that are connected to these terminals.

The ultrasound probe 2 acts as an acoustic sensor which generates and emits ultrasound waves (about 1 to 30 MHz in this embodiment) toward a subject such as a living body, receives echoes of the emitted ultrasound waves, which are reflected off the subject, and converts the echoes into electric signals. The ultrasound probe 2 includes a transducer array 210, i.e. an array of transducers 21 for transmitting and receiving ultrasound waves, and a cable 22. The cable 22 has a connector (not shown) for the main unit 1, at its one end. The ultrasound probe 2 is detachably connected to the main unit 1 via the cable 22.

The transducer array 210 is an array of transducers 21. Each transducer 21 includes a piezoelectric element and electrodes on two sides. An electric charge appears on these electrodes when the piezoelectric element is deformed (expansion and contraction). The array of transducers 21 is, for example, a one-dimensional array. Voltage pulses (pulse signals) supplied to the transducers 21 generate an electric field in each of the piezoelectric elements. The electric field deforms the piezoelectric element, which generates and emits ultrasound waves. The sound pressure of ultrasound waves of predetermined frequencies incident on each of the transducers 21 causes a vibration or oscillation in each piezoelectric element in the thickness direction. As a result, an electric charge with an amount in response to the oscillation appears at each end in the thickness direction of the piezoelectric element. This induces an electric charge with an amount, in response to that of the electric charge on the electrode of the piezoelectric element. In this embodiment, the piezoelectric elements are composed of a ferroelectric material. The intensity of the electric field generated in the ferroelectric material during transmission and reception of ultrasound waves is smaller than that of the coercive electric field of the ferroelectric material.

The ferroelectric material is, for example, lead zirconate titanate (PZT) in the form of a thin film (typically less than 10 μm, preferably less than 1 μm). Alternatively, any other ferroelectric material may be used. Examples of such ferroelectric materials include ferroelectric materials with a perovskite structure, a tungsten bronze structure, and a bismuth layered structure, organic ferroelectric materials, such as polyvinylidene fluoride (PVDF) and PVDF copolymers, and composites of these materials. These ferroelectric materials are of a multi-domain structure and/or of a polycrystalline structure under normal conditions.

Figure 3:
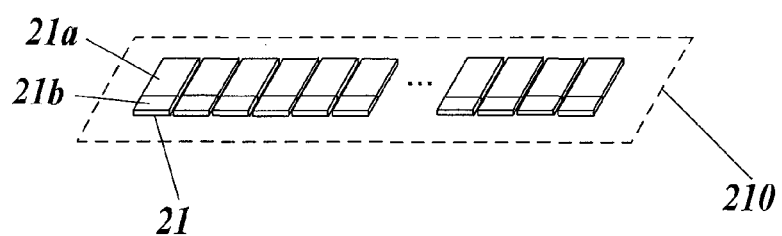
FIG. 3 shows an array of transducers in an ultrasound probe.

FIG. 3 shows an arrangement of the transducers 21 in the transducer array 210 included in the ultrasound probe 2 according to this embodiment.

The ultrasound probe 2 according to this embodiment includes, for example, 192 units of the transducers 21 arranged one-dimensionally in the direction of scanning in the transducer array 210. Alternatively, the transducers 21 may be disposed in a two-dimensional array. Any number of transducers 21 can be disposed. The ultrasound probe 2 may adopt electrical scanning or mechanical scanning. The scanning may be any of linear scanning, sector scanning, and convex scanning. Any frequency range in which the ultrasound probe 2 receives ultrasound waves can be set.

The ultrasound diagnosis apparatus S may be configured to allow any one of the multiple ultrasound probes 2 to be connected to the main unit 1 depending on the subject undergoing diagnosis.

The size of the piezoelectric element in each transducer 21 is determined according to the received frequency band of ultrasound waves. Each piezoelectric element consists of two areas 21a and 21b. Thus, the areas 21a and 21b have individual polarizations.

Ultrasound-wave receiving circuits in the ultrasound probe 2 according to this embodiment will now be described.

Figure 4A:
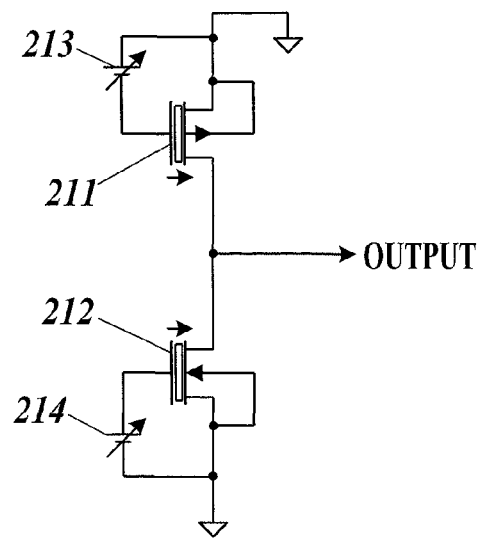
FIG. 4A shows a circuit for receiving ultrasound waves.

FIG. 4A shows an ultrasound-wave receiving circuit in this embodiment.

The transducers 21 of the ultrasound probe 2 according to this embodiment are produced in the form of semiconductor chips by a thin film forming process. An ultrasound-wave receiving circuit, i.e. each transducer 21, provided in a semiconductor chip includes two circuit segments equivalent to single-transistor type field-effect transistors (1T-FETs), which are connected each other. Each 1T-FET has a ferroelectric thin film (a piezoelectric thin film) in addition to a gate insulating film and a silicon dioxide thin film. In this embodiment, the drain of each p-channel receiving circuit block 211 equivalent to a p-channel FET and the drain of each n-channel receiving circuit block 212 equivalent to a n-channel FET are connected at an output. The source of the p-channel receiving circuit block 211 and the source of the n-channel receiving circuit block 212 are separately grounded.

In other words, on each ultrasound-wave receiving circuit according to this embodiment, a first FET is provided instead of a drain resistor which is otherwise connected to the drain of a second FET. The ultrasound-wave receiving circuit has no source resistor connected to the source. Instead, each source of the FETs is directly grounded. Thus, the circuit includes no resistance element, which relatively occupy the space (volume) in a semiconductor chip. The circuit has a pattern that provides single source ground amplification as a whole to receive output signals from both the receiving circuit blocks 211 and 212 in a push-pull manner. This enables each circuit to efficiently increase its receiving sensitivity relative to its area for receiving ultrasound waves.

The sources and gates of the p-channel receiving circuit block 211 and the n-channel receiving circuit block 212 are connected via bias power supplies 213 and 214, respectively. A ferroelectric thin film used in each p-channel receiving circuit block 211 corresponds to the area 21a. A ferroelectric thin film used in each n-channel receiving circuit block 212 corresponds to the area 21b. In this embodiment, these ferroelectric thin films, i.e. the areas 21a and 21b, exhibit similarly oriented polarization. Each of the areas 21a and 21b, i.e., the ferroelectric thin films, may be further segmented into a plurality of blocks, and disposed like tiles. The areas 21a and 21b are not necessarily provided immediately above the respective channel regions provided that an electric field appears in each of the channel regions in response to charges induced in the areas 21a and 21b.

The ultrasound probe 2 according to this embodiment includes enhancement types of p-channel receiving circuit blocks 211 and n-channel receiving circuit blocks 212. When the circuit blocks 211 and 212 receive ultrasound waves, the bias power supplies 213 and 214 apply bias voltages to the respective gate electrodes. Thus, even if no electric field appears (no expansion and contraction occur) in each ferroelectric thin film during the reception of ultrasound waves, the p-channel receiving circuit blocks 211 and the n-channel receiving circuit blocks 212 outputs signals.

If the ultrasound probe 2 includes depletion types of p-channel receiving circuit blocks 211 and n-channel receiving circuit blocks 212, no bias voltage is required during the reception of ultrasound waves. It is, however, preferable that the bias power supplies 213 and 214 apply respective reverse gate voltages because such circuit blocks output signals even during no reception of ultrasound waves.

The bias power supplies 213 and 214 are also used to apply predetermined voltages to the respective ferroelectric thin films. The predetermined voltages should be greater than or equal to the voltages in the coercive electric fields of the ferroelectric thin films. This enables the polarization at each ferroelectric thin film to be individually set.

A circuit for applying the predetermined voltage (polarization voltage applying circuit) and a circuit for applying the bias voltage (bias voltage applying circuit) can be disposed independently to each other. Since the both voltages are not applied at the same time, a single circuit can be shared. On the contrary, sharing a single circuit can reduce circuit components.

Signals output from each ultrasound-wave receiving circuit are sent to the receiver 13 and the signals are amplified in voltage by the amplifier with an appropriate amplification factor. The amplified signals then undergo A/D conversion, phasing addition, and other processes. Alternatively, signals may undergo accumulation, transfer, phasing, and adding up of electric charges, and then amplification and A/D conversion.

Figure 5:
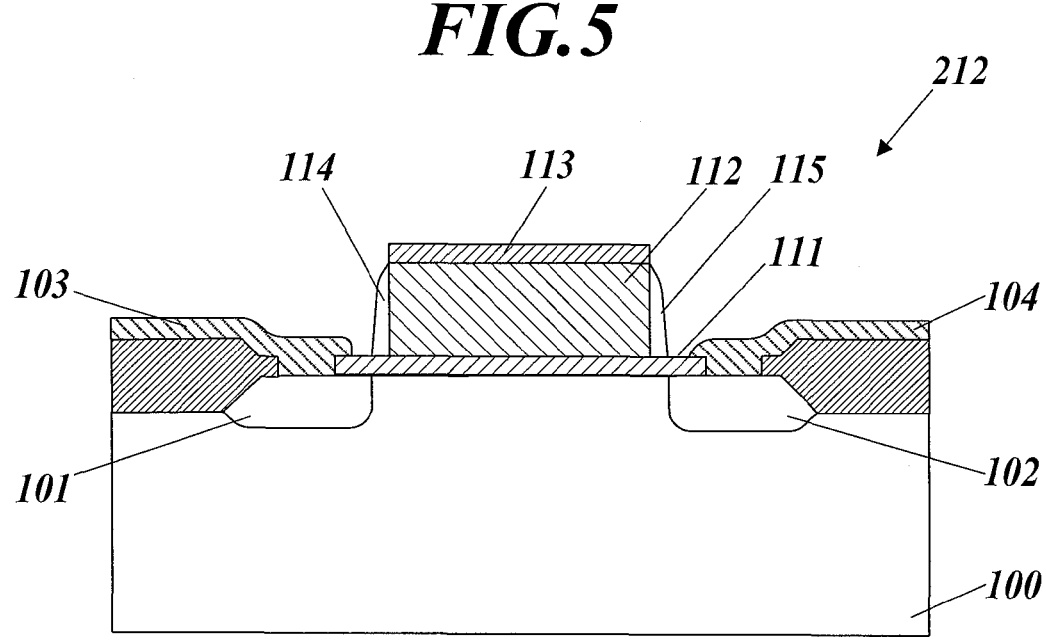
FIG. 5 is a cross-sectional view of an n-channel receiving circuit block.

FIG. 5 is a cross-sectional view of the n-channel receiving circuit block 212.

As is well known, the p-channel receiving circuit block 211 and the n-channel receiving circuit block 212 have opposite polarity in their respective areas. Except for the difference in polarity, the both circuit blocks have similar configurations. Thus, redundant descriptions on the p-channel receiving circuit block 211 are omitted.

The n-channel receiving circuit block 212 in the transducer 21 according to this embodiment has a laminated structure including a semiconductor substrate 100, a gate insulating film 111, a ferroelectric thin film 112, and a gate electrode 113, in sequence. Both sides of the ferroelectric thin film 112 are provided with side walls 114 and 115. The upper face of the semiconductor substrate 100 is overlaid with a source region 101 and a drain region 102 which are separated by an area (a channel region) below the gate electrode 113. The source region 101 and the drain region 102 are connected to metal leads 103 and 104, respectively.

The semiconductor substrate 100 is a p-type silicon substrate. Negative ions of chemical elements, such as phosphorus and arsenic, are injected into the semiconductor substrate 100 to form an extension region (a conductive region), the source region 101, and the drain region 102.

The source region 101 is grounded via the metal lead 103. The drain region 102 is connected to the output for signals via the metal lead 104. The bias power supply 214 is connected to the gate electrode 113 so that the bias power supply 214 applies a predetermined bias voltage across the gate and the source via the gate electrode 113. The bias power supply 214 also applies a predetermined voltage to the ferroelectric thin film 112. The predetermined voltage should be greater than or equal to a voltage in the coercive electric field of the ferroelectric thin film 112. As a result, the polarization of the ferroelectric thin film 112 varies in response to the predetermined voltage.

The bias power supply 214 may be not necessarily integrated with the n-channel receiving circuit block 212 including the semiconductor substrate 100. As long as the semiconductor substrate 100 has a circuit for applying voltages, the bias power supply 214 may be provided externally, for example, at the main unit 1 to supply voltages. The external bias power supply 214 can produce and supply a desired voltage without constraints such as size, weight, and heating value, which are essential for a bias power supply provided inside the ultrasound probe 2. An external bias power supply, however, requires any countermeasure to prevent of noise contamination of output signals.

Ultrasound waves incident on the ferroelectric thin film 112 under normal conditions generate a charge with an amount in response to the intensity of the ultrasound waves (sound pressure) and the original polarization on each side (each surface) of the ferroelectric thin film 112. The generated charges and the predetermined bias voltage cause an electric field to generate in the channel region between the source region 101 and the drain region 102 on the semiconductor substrate 100. Variations in the conduction state of the channel region, i.e. the amount of charges flowing between the source and the drain cause signals to be output through the drain region 102.

A ferroelectric thin film 112 and a gate electrode 113 are deposited on the semiconductor substrate 100 by a sputtering (physical vapor deposition (PVD)) process, a sol-gel process, a chemical-vapor deposition (CVD) process, or any other process. The ferroelectric thin film 112 and the gate electrode 113 are then formed by, for example, photo etching of the thin films through a photoresist layer or any other photomask tailored to the structures of the ferroelectric thin film 112 and the gate electrode 113. After an insulating film of, for example, silicon dioxide ($SiO_2$) is deposited on the semiconductor substrate 100, the ferroelectric thin film 112, and the gate electrode 113 by a chemical-vapor deposition (CVD) process or any other process, the insulating film is etched into side walls 114 and 115. The source region 101 and the drain region 102 are formed by self-alignment by ion injection through the gate electrode 113 and the side walls 114 and 115 functioning as photomasks. The metal leads 103 and 104 are then provided so as to be connected to the gate electrode 113, the source region 101, and the drain region 102.

The p-channel receiving circuit block 211 and the n-channel receiving circuit block 212 may be integrated on a single semiconductor substrate 100.

As described above, since the size of the ferroelectric thin film 112 is determined depending on the receiving frequencies, it is difficult to change the size. Contrarily, other elements on the semiconductor substrate 100 can be downsized. In most cases, the size of the ferroelectric thin film 112 is larger than the sizes of the other elements in each of the receiving circuit blocks 211 and 212. Thus, the surface area and the thickness of the ferroelectric thin film 112 are determined depending on the reception frequencies of ultrasound waves are, while the length of the channel between the source region 101 and the drain region 102 is appropriately maintained. If the area of the ferroelectric thin film 112 is larger than the gate insulating film 111 and the channel region, the film 112 should be insulated therefrom with insulating films. In this case, the ferroelectric thin film 112 and the other elements may be formed in any order.

Since each transducer 21 in the ultrasound probe 2 includes a ferroelectric thin film 112, the ferroelectric layer is distributed evenly. Thus, the ferroelectric thin films 112 exhibit polarizations with reliable accuracy in response to the intensities of incident ultrasound waves. Also, such a thin film can be activated at a sufficiently low voltage for causing the coercive electric field necessary for polarity reversal. As a result, even after the circuit of the transducer 21 is formed, a voltage can be easily applied to the ferroelectric thin films 112 to change the polarity.

In this case, the thickness of the ferroelectric thin films 112 in each of the receiving circuit blocks 211 and 212 should be determined so that the withstand voltages at portions, for example, the dielectric breakdown voltage of the gate insulating film 111, withstand voltage between the drain and the source, withstand voltage between the p- and n-wells, and withstand voltage between the wells and the semiconductor substrate 100, are larger than the maximum voltage applied to the ferroelectric thin film 112 to generate an coercive electric field. Under normal conditions, the withstand voltages at these portions range from ten to several tens of volts. Thus, the voltage for causing the coercive electric field should be smaller than these values. The coercive electric field is approximately 1 MV/m although it depends on the ferroelectric material, the proportion of the components, the crystal system, and other factors. In order to achieve a voltage for causing the coercive electric field of less than the withstand voltage, the thickness of the ferroelectric thin film 112 should be 1 μm or less in view of the influence of the thickness of the gate insulating film 111.

The applied voltage for transmitting ultrasound waves through the ferroelectric thin film 112 can be lowered to an appropriate value depending on the thickness of the thin film 112 on condition that the lowered voltage is less than the voltage for causing the coercive electric field, brings about no change in the polarization, and generates a negligible level of heat.

A ferroelectric thin film 112 of a multi-domain structure and/or of a polycrystalline structure in the transducer 21 according to this embodiment can receive ultrasound waves not only when each region of the multi-domain structure and/or of the polycrystalline structure is polarized in a uniform direction but also when the polarizing direction in each region is not uniform in varying degrees. When ultrasound waves enter the ferroelectric thin film 112 with a uniform polarization direction, the entire ferroelectric thin film 112 is deformed in response to the sound pressure of the ultrasound waves, like an ordinary piezoelectric element. As a result, electric charges appear at each side in response to the deformation. When ultrasound waves enter the ferroelectric thin film 112 with the polarizing direction in each region varying in an utmost degree, no expansion or contraction occur in the ferroelectric thin film 112 as a whole. In other words, no charge appears at each end because of no overall deformation. The sensitivity of receiving ultrasound waves can be adjusted by setting a variation in polarizing direction to middle degrees.

The polarization of the ferroelectric thin film 112, however, does not vary in proportion to the strength of the electric field appearing in the ferroelectric thin film 112. This problem can be resolved by referring a table of the correspondence between target polarizations and electric fields (applied voltages) essential for the target polarizations preliminarily stored on the HDD of the controller 15 or any other storage. The current polarization of the ferroelectric thin film 112 is changed to a desired level with reference to this table to obtain an applied voltage required for the desired polarization, and supplying the applied voltage from the bias power supply 214 to the gate electrode 113. Alternatively, a table listing only the correspondence between a specified polarization and target polarizations may be stored so that the current polarization is changed to a desired polarization by way of the specified polarization.

[First Variation]

Figure 4B:
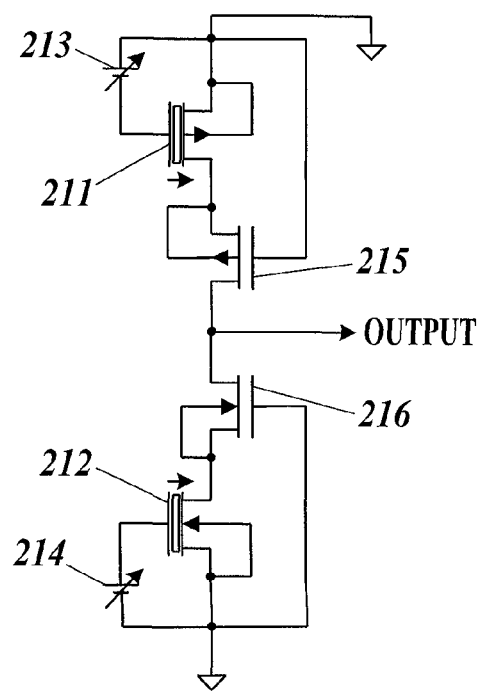
FIG. 4B shows a variation of the circuit for receiving ultrasound waves.

FIG. 4B shows a first variation of the ultrasound-wave receiving circuit in the ultrasound probe 2 according to this embodiment.

With reference to FIG. 4B, a ultrasound-wave receiving circuit included in an ultrasound probe 2, which is a variation of the circuit of FIG. 4A, further includes a p-channel MOSFET 215 cascade-connected to the p-channel receiving circuit block 211 and a n-channel MOSFET 216 cascade-connected to the n-channel receiving circuit block 212. In this configuration, a cascade bootstrap is applied to each circuit block of an FeRAM structure for receiving ultrasound waves. This provides an improvement in receiving sensitivity characteristics at high frequencies, i.e. frequencies for receiving ultrasound waves.

[Second Variation]

Figure 6:
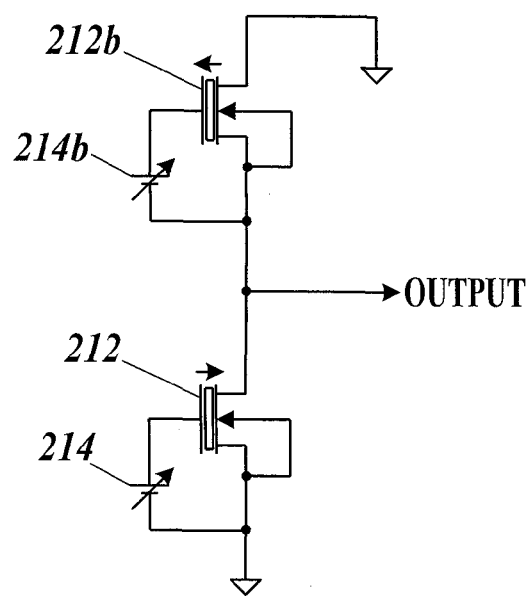
FIG. 6 shows a circuit for receiving ultrasound waves in a second variation.

FIG. 6 shows a second variation of the ultrasound-wave receiving circuit in the ultrasound probe 2.

An ultrasound-wave receiving circuit of the second variation includes two n-channel receiving circuit blocks 212 and 212b. Respective sources and gates of the n-channel receiving circuit blocks 212 and 212b are connected via bias power supplies 214 and 214b, respectively. The ferroelectric thin films in the n-channel receiving circuit blocks 212 and 212b are polarized in mutually opposite directions.

In the n-channel receiving circuit blocks 212 and 212b exhibiting opposite polarizations each other, the electric field appearing in the ferroelectric thin film of a first ferroelectric memory is strengthened in the forward direction (a direction in which a channel region is switched to a conduction state) in response to the amount of the contraction of the ferroelectric thin film due to the sound pressure and is weakened in the forward direction in response to the expansion of the ferroelectric thin film. In contrast, the electric field appearing in the ferroelectric thin film of a second ferroelectric memory is strengthened in the opposite direction in response to the contraction of the ferroelectric thin film due to the sound pressure and is weakened in the opposite direction in response to the expansion of the ferroelectric thin film. The voltages appropriately applied to the first and second ferroelectric memories produce an electric field strengthened by contraction in the forward direction and an electric field strengthened by expansion in the forward direction in the respective channel regions.

The n-channel receiving circuit block 212 includes a drain connected to an output and a source connected to aground while the n-channel receiving circuit block 212b includes a source connected to the output and a drain connected to a ground. Thus, if the ferroelectric thin film contracting in the first ferroelectric memory causes electric current to flow in an outlet (source-to-drain) direction, the ferroelectric thin film expanding in the second ferroelectric memory causes electric current to flow in an inlet (drain-to-source) direction. Consequently, these two n-channel receiving circuit blocks 212 and 212b output signals in a push-pull manner.

The n-channel receiving circuit block 212 acts as a common-source amplifier, and the n-channel receiving circuit block 212b is a source follower. As a result, output signals become uneven as the amplification factor changes. Thus, the polarizations and/or bias voltages applied to the gate electrodes should be adjusted such that the amplification factors are kept at 1. Since signals output from these two circuit blocks are complementary to each other, signals can be acquired with double sensitivity on the whole.

As described above, the acoustic sensor of the ultrasound probe 2 according to this embodiment includes the transducers 21. Each transducer 21 includes the p-channel receiving circuit block 211 equivalent to a p-channel ferroelectric memory and the n-channel receiving circuit block 212 equivalent to an n-channel ferroelectric memory. The p-channel receiving circuit block 211 and the n-channel receiving circuit block 212 each has a laminated structure including the semiconductor substrate 100, a ferroelectric thin film, and the gate electrode, in sequence. The conduction state of each channel region varies in response to the sound pressure incident on the ferroelectric thin film. The p-channel receiving circuit block 211 and the n-channel receiving circuit block 212 are connected at their drains through which signals are output.

In this configuration, one of the receiving circuit blocks acts as a drain resistor with respect to the other receiving circuit block. The circuit blocks each function as a common-source amplifier, and the two circuit blocks output integrated and amplified signals. These circuit blocks also output complementary signals in response to the expansion and contraction of the ferroelectric thin films caused by ultrasound vibration. Consequently, this acoustic sensor can efficiently acquire signals in response to the reception of ultrasound waves from the ferroelectric thin films at high precision and high sensitivity relative to the surface area of the semiconductor substrate 100.

The receiving circuit block without any resistance element can have smaller dimensions as compared to a semiconductor chip which includes a resistance element occupying a larger space.

The semiconductor chip of each transducer 21 includes a circuit for applying predetermined bias voltages to the respective ferroelectric thin films through the bias power supplies 213 and 214. The bias voltages are determined such that the strengths of signals output from the p-channel receiving circuit block 211 and the n-channel receiving circuit block 212 are complementary with respect to incident sound pressure. As a result, the transducer 21 can output well-balanced signals at high sensitivity. This enables the ultrasound diagnosis apparatus S to readily process the signals and make an appropriate diagnosis.

Each ferroelectric thin film is composed of a ferroelectric material, such as PZT. Polarizations at the ferroelectric thin films are determined such that the strengths of the respective output signals in response to sound pressure are complementary to each other. Thus, the transducer 21 can output well-balanced signals at high sensitivity with no further correction. This enables the ultrasound diagnosis apparatus S to readily process the signals for an appropriate diagnosis.

The semiconductor chip of each transducer 21 includes a circuit for applying a predetermined voltage which is greater than or equal to a voltage in the coercive electric field of the ferroelectric thin film to vary the polarization of the ferroelectric thin film. The ferroelectric thin film is formed such that the voltage in the coercive electric field is less than the withstand voltages at portions in the semiconductor chip. Thus, even after the transducers 21 and the transducer array 210 are formed, the predetermined voltage can be applied to each ferroelectric thin film to adjust the polarity of the ferroelectric thin film as needed. Consequently, the alignment, weighting for reception, and formation of a reception window can be easily performed among the transducers 21 whenever necessary.

A single circuit can be shared for application of the bias voltage and application of the predetermined voltage. Thus, no redundant electrical lead line is disposed on the transducer 21. In other words, constraints on the circuit placement are eased, and the generation and the influence of noise can be curbed.

The p-channel receiving circuit block 211 and the n-channel receiving circuit block 212 are equivalent to two FETs each having a piezoelectric thin film between the gate electrode and the channel region. The circuit blocks 211 and 212 are connected at their sources, through which signals are output, so that each circuit block functions as a common-source amplifier. This configuration eliminates the need for resistance and constant current circuit elements, which are irrelevant to the reception of ultrasound waves, but occupy the space. This configuration also allows the circuit blocks to acquire signals with mutual complementarity and a high efficiency.

The ultrasound probe 2 of an acoustic sensor including the transducers 21 described above can receive ultrasound waves with efficiency and high sensitivity.

The scope of the present invention should not be limited to the embodiment described above, and should include various modifications and variations.

The present invention is applied to an acoustic sensor including ferroelectric thin films in the embodiment described above, nevertheless, the present invention can also be applied, for example, to an acoustic sensor including ordinary piezoelectric thin films without ferroelectric characteristics. In this case, desired polarization is not kept, that is, the piezoelectric thin films exhibit no polarization when no signal enters; hence, such a configuration requires appropriate application of bias voltages across the gates and the sources through bias power supplies 213 and 214, or use of depletion types of FETs.

In the case of use of the ferroelectric thin films, polarizations may be adjusted only after a long-term change due to deterioration over time and other time-related factors. Ordinarily, apodization and window setting may be carried out by varying the amplification factor of the amplifier, or changing switch settings on the switching element.

In the embodiment described above, a gate oxide film is disposed between the ferroelectric thin film and a silicon substrate. Like a MOSFET structure, a ferroelectric thin film may be directly disposed on a silicon substrate with no gate oxide film therebetween.

In the embodiment described above, the conduction state is controlled via FETs. The FETs may be replaced with bipolar transistors. In this case, an npn transistor and a pnp transistor are combined. Instead of sources, the emitters of the two transistors are grounded. Charges (electric currents) in response to the reception of ultrasound waves flow into the bases. Signals are output from the collectors at which the two transistors are connected each other. Withstand voltages, which should be larger than a voltage for causing the coercive electric field, include, for example, those at portions between any two of the base, the emitter, and the collector regions.

In the embodiment described above, the 1T-FETs are exemplified which act as common-source amplifiers, in which the sources are grounded and the gates accept input signals in response to incident ultrasound waves. The 1T-FETs may be replaced with a combination of two 1T1C memory cells that act as common-gate amplifiers, in which the gates are grounded and charges in response to charges generated in the ferroelectric capacitors by incident ultrasound waves are induced to the sources.

In the embodiment described above, signals are amplified and output through a combination of two transistors (receiving circuit blocks) having ferroelectric thin films. The two transistors may be replaced with at least two, for example, four transistors that are symmetrically disposed and output signals with mutual complementarity.

In the first variation of the embodiment described above, the MOSFETs 215 and 216 are bootstrap-connected to the receiving circuit blocks 211 and 212, respectively, in a cascade arrangement to improve the frequency characteristics of output signals at high frequencies. The MOSFETs 215 and 216 may be just cascaded. Alternatively, the MOSFETs 215 and 216 may be replaced with bipolar transistors.

The embodiment described above exemplifies an ultrasound probe according to an ultrasound diagnosis apparatus for medical use. The ultrasound diagnosis apparatus may be one for diagnosis of the interior of buildings and structures. In this case, the ultrasound probe which acts as an acoustic sensor for transmission and reception of ultrasound waves may be provided anywhere other than the outside of the main unit, and may be integrated with the main unit.

The acoustic sensor or transducer according to the present invention may be applied to any device that simply measure the intensity of receiving ultrasound waves, other than ultrasound diagnosis apparatuses. In such a case, a single acoustic sensor may be provided instead of a plurality of acoustic sensors.

The ultrasound probe in the embodiment described above receives ultrasound waves at frequencies ranging from 1 to 30 MHz. The present invention can, however, be applied to any acoustic sensor receiving sound waves at frequencies at which a piezoelectric component in the acoustic sensor which is fabricated by a thin-film forming process can receive sound waves.

The scope of the present invention should include various modifications and variations of specific compositions, configurations and detailed dispositions shown in the embodiment described above without deviating from the gist of the present invention.

The entire disclosure of Japanese Patent Application No. 2014-049720 filed on Mar. 13, 2014 including description, claims, drawings, and abstract are incorporated herein by reference in its entirety.

What is claimed is:

1. An acoustic sensor comprising:
    a semiconductor chip comprising at least two transistors, wherein each of the at least two transistors is connected to a piezoelectric thin film which is layered in the transistor, and the piezoelectric thin films are directly or indirectly disposed over a semiconductor substrate such that a conduction state of each of the at least two transistors varies in response to a pressure of sound waves incident on the piezoelectric thin films, and wherein the at least two transistors are connected to constitute a single amplifier circuit so as to add up and amplify a signal with a strength in response to the conduction state of each of the at least two transistors, and output the amplified signal.

2. The acoustic sensor of claim 1, wherein the semiconductor chip further comprises a circuit which applies a predetermined bias voltage to each of the piezoelectric thin films, and the bias voltage is determined such that the strength of a signal output through each of the at least two transistors is complementary with respect to the pressure of the sound waves incident on each of the piezoelectric thin films.

3. The acoustic sensor of claim 1, wherein each of the piezoelectric thin films is formed of a ferroelectric material, and polarizations of the piezoelectric thin films are determined such that the strengths of the signals in response to the respective pressures of the sound waves incident on the respective piezoelectric thin films are complementary.

4. The acoustic sensor of claim 3, wherein the semiconductor chip further comprises a circuit which applies a predetermined voltage to alter the polarization of each of the piezoelectric thin films, in which the predetermined voltage is greater than or equal to a voltage in a coercive electric field of each of the piezoelectric thin films, and wherein the voltage in the coercive electric field of each piezoelectric thin film is less than a withstand voltage of each of the at least two transistors.

5. The acoustic sensor of claim 4, wherein the circuit also applies a predetermined bias voltage to each of the piezoelectric thin films, and the bias voltage is determined such that the strength of a signal output through each of the at least two transistors is complementary with respect to the pressure of the sound waves incident on each of the piezoelectric thin films.

6. The acoustic sensor of claim 1, wherein the at least two transistors are field-effect transistors each including the piezoelectric thin film between a gate electrode and a channel region, and wherein drains of the field-effect transistors are connected to each other such that each field-effect transistor constitutes a common-source amplifier circuit, and signals are output through the drains.

7. An ultrasound probe comprising the acoustic sensor of claim 1.

* * * * *